United States Patent [19]
Chimenti

[11] 4,236,071
[45] Nov. 25, 1980

[54] DETECTION OF URANIUM BY LIGHT INDUCED LUMINESCENCE

[75] Inventor: Robert J. L. Chimenti, Short Hills, N.J.

[73] Assignee: Exxon Research & Engineering Co., Florham Park, N.J.

[21] Appl. No.: 40,900

[22] Filed: May 21, 1979

Related U.S. Application Data

[63] Continuation-in-part of Ser. No. 832,836, Sep. 13, 1977, abandoned.

[51] Int. Cl.$^2$ .............................................. G01V 5/00
[52] U.S. Cl. .................................. 250/253; 250/461 R
[58] Field of Search ............ 250/253, 302, 372, 461 R

[56] References Cited

U.S. PATENT DOCUMENTS

| | | | |
|---|---|---|---|
| 3,043,908 | 7/1962 | Madsen ............................. | 250/253 X |
| 3,736,428 | 5/1973 | Monroe ................................ | 250/253 |
| 3,961,187 | 6/1976 | Barringer ............................. | 250/301 |

*Primary Examiner*—Davis L. Willis
*Attorney, Agent, or Firm*—D. W. Collins; Jack Matalon

[57] ABSTRACT

A method for the detection and identification of uranium bearing materials in media found in nature such as rocks, soils, surface and sub-surface waters, vegetation, or in material which has been subjected to physical or chemical processing comprises the steps of: irradiating the media with a light, having a single wavelength or narrow band of wavelengths in the range of about 2400 to 5000Å for a time equal to or less than about 100 microseconds; waiting for a period of time, which is dependent on twice the distance of the light-source to the irradiated medium, followed by measurement of the intensity and decay time of the luminescent light emitted by the irradiated media in a narrow spectral range, having a wavelength greater than the wavelength of the light used to irradiate the media. The method is useful for remote geochemical prospecting for uranium using laser induced luminescence and in monitoring products and effluents from installations processing or utilizing uranium compounds, such as in elemental or isotopic separation, purification, recovery and ore beneficiation.

16 Claims, 7 Drawing Figures

DETECTION OF URANIUM BY LIGHT INDUCED LUMINESCENCE

CROSS-REFERENCE TO RELATED APPLICATIONS

This is a continuation-in-part application of Ser. No. 832,836, filed Sept. 13, 1977, now abandoned.

BACKGROUND OF THE INVENTION

1. Field of the Invention

This invention relates to methods for the detection and identification of uranium bearing materials in media, in the form found in nature such as in rocks, soils, clays, streams and lakes, decayed organic matter, vegetation, subsurface water, and films or in media which contain uranium compounds or have come in contact with uranium compounds such as products and effluents from installations, processing or utilizing uranium compounds such as in elemental or isotopic separation, purification, recovery and ore beneficiation. One method utilizes a time-delayed measurement, in one or more narrow spectral ranges, of the intensity and decay time of the luminescence emitted by hexavalent uranyl ions when irradiated by light from a source having a wavelength in the range of about 2400 to 5000 Å for a duration equal to or less than about 100 microseconds.

2. Prior Art

When certain materials are irradiated with ultraviolet light, i.e. light having a wavelength in the range of about 1800 to 3700 Å, and after cessation of the irradiation, photons are emitted from the material, the material is said to exhibit luminescence. By definition in the prior art, if the luminescence ceases on termination of the irradiation, the phenomenon is termed fluorescence; if the luminescence persists after termination of irradiation, the phenomenon is termed phosphorescence. These definitions were made at a time when observations of the persistence of luminiscence was made with the unaided eye, but with the development of instruments which can measure the persistance of luminescence in nanoseconds after termination of irradiation, it is now known that many materials, in particular, uranium-bearing substances comprising hexavalent uranyl ions which have been characterized in the literature as fluorescent substances, emit luminescence for as long as 1000 microseconds after termination of light excitation.

Since the term "fluorescence" and "phosphorescence" have been standardized in the literature for more than 100 years, the more general term "luminescence" will be used herein to describe the emission of light from a material after termination of light excitation.

Deposits of uranium minerals, for example originating from igneous rocks or volcanic tuff which have eroded, are solubilized and carried by oxidizing surface waters to lower strata where they are redeposited, for example, in sandstones by reducing agents such as pyrite, hydrogen sulfide, or hydrocarbons. Where such deposits have surface expressions and have been reoxidized in part, ordinary methods for prospecting in the field for uranium minerals have depended in the past on the luminescence that is observed when these minerals are illuminated with ultraviolet light from a portable lamp.

A major difficulty in the use of this method is that the terrain must be readily accessible, and a great many nonuranium bearing minerals, organics and other natural substances luminesce when excited in the same spectral range as uranium-bearing substances or have luminescence wavelengths which are common to the emission from uranium-bearing substances and thus obscure their luminescence, especially when these substances are present in low concentrations in the material under examination.

More recently, remote detection of substances which luminesce has been proposed by means of Fraunhofer line-depth discrimination using sunlight and air-borne LIDAR (See: W. R. Hemphill et al, 6th Sympos. on Remote Sensing, Ann Arbor, Mich. Oct. 19, 1969); Continuous-Wave Laser Flurometer (See O'Neil et al, Water Science-Inland Waters Directorate, Canada). In addition, U.S. Pat. No. 3,961,187 discloses a method for detecting oil seepages at sea from an aircraft using a laser beam, and the UA-3 uranium analyser marketed by Scintrex Limited of Canada uses a laser in the ultraviolet range and an undisclosed proprietary reagent for the determination of uranium in a water sample contained in a quartz cell.

SUMMARY OF THE INVENTION

In distinction to the methods for prospecting for uranium-bearing substances known and described in the prior art, I have now found that uranium-bearing substances, particularly those in which the uranium is present as hexavalent uranyl ion ($UO_2++$), may be detected from a remote observation point such as airborne means as from an airplane or helicopter, by illuminating a target area of the terrain with light having a single wavelength or narrow range of wavelengths in the range of about 2400 to 5000 Å, preferably coherent light emitted by a laser, for a period of time of up to about 100 microseconds, waiting for a period of time equal to twice the propagation time required for the light beam to travel from the light source to the target area plus about 50 microseconds, and then measuring the intensity and the decay time of the luminescence emitted from the target area in a single or multiple narrow spectral region having a wavelength greater than the wavelength of the light beam used to illuminate the target. Further discrimination against non-uranium fluorescence is to restrict the excitation wavelength to the spectral region between about 3700 and 4500 Å, although lower wavelengths between about 2800 and 3500 Å may also be employed.

DETAILED DESCRIPTION OF THE INVENTION

Figure 1:
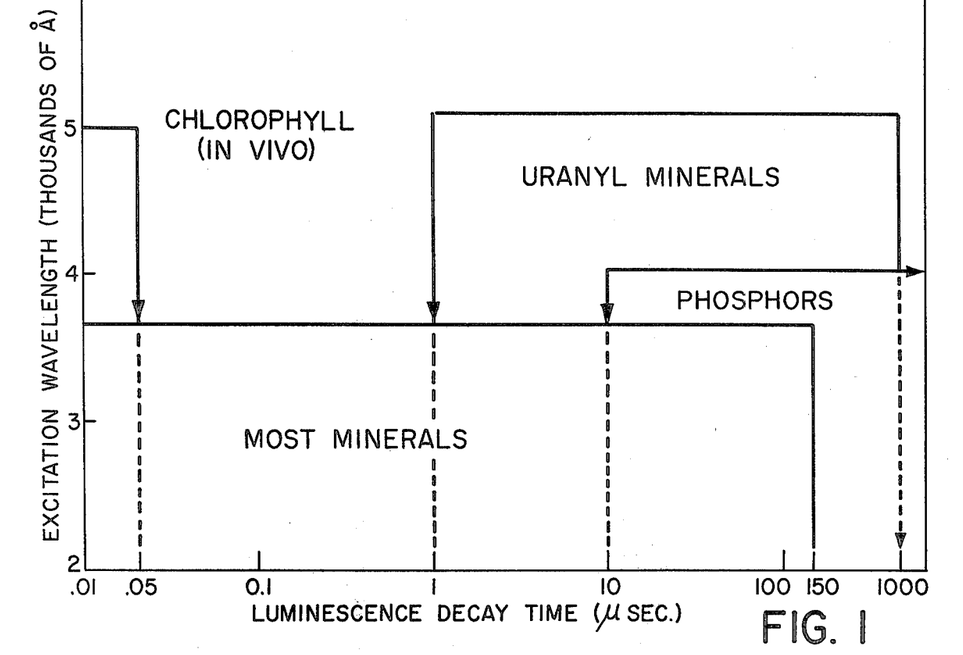
FIG. 1, on coordinates of excitation wavelength (Å) and time ($\mu$sec) depicts regions of luminescence decay for a variety of materials.

FIG. 1 shows the regions of luminescence decay times and excitation wavelengths for a variety of minerals, phosphors, uranyl minerals, and chlorophyll in living plants. It will be noted that most non-uranium minerals absorb light with wavelengths below 3700 Å and exhibit luminescence decay times which are generally less than 150 microseconds. Similarly, phosphors strongly absorb light with wavelengths below 3700 Å, although I have observed that some phosphors such as Willemite ($Zn_2SiO_4:Mn^{2+}$) can exhibit strong luminescence when excited by light having a wavelength of 4250 Å. Willemite, for example, when excited with light having a wavelength of 4250 Å for a time of 0.008 microseconds exhibits a luminescence decay time of 1.2 milliseconds. Other phosphors, such as the mixed sulfides of calcium, strontium and barium luminesce in excess of minutes. In addition, the spectra of the luminescence emitted by phosphors are generally featureless and extend over several hundred Angstroms.

Chlorophyll is distinguished by strong absorption bands in the visible range or up to 5000 Å with a luminescence in the region of red wavelengths which persists for less than 50 nanoseconds after termination of illumination.

Tests made by me on a variety of minerals comprising the hexavalent uranyl ion have demonstrated that when these minerals are irradiated for less than 100 microseconds with laser radiation having a wavelength of 4250 Å, the luminescence emitted from the mineral exhibits decay times in the range of about 50 to 1000 microseconds. The spectra of the luminescence are highly structured and are contained in the range of 5000 Å to 6000 Å.

Figure 2:
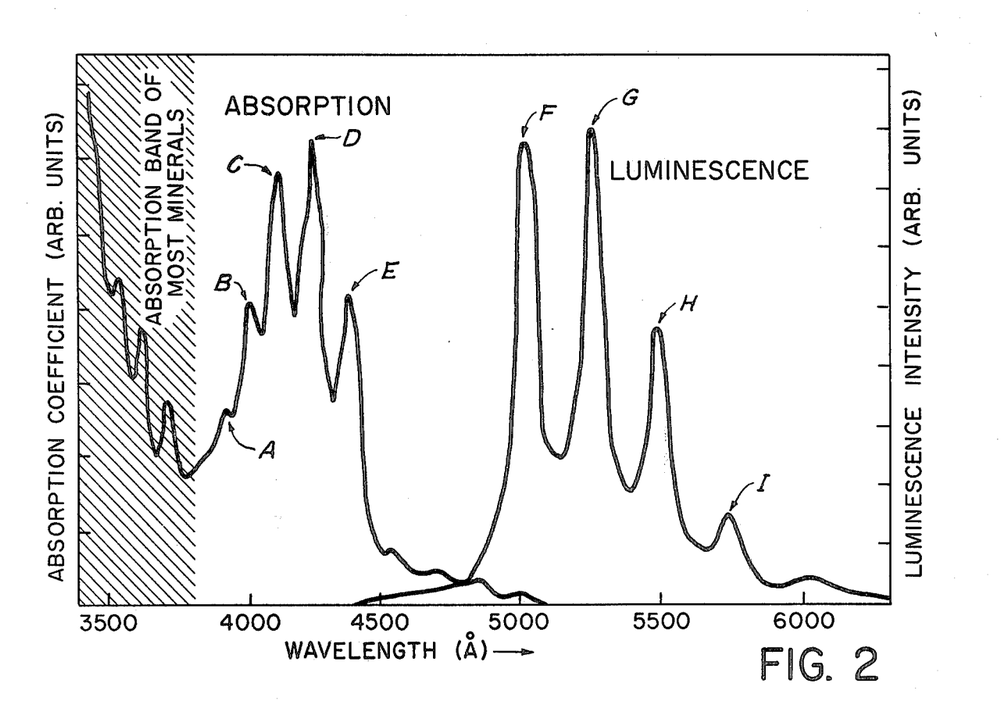
FIG. 2, on coordinates of intensity and wavelength (Å), depicts the absorption and luminescence spectra of autunite.

FIG. 2 shows the absorption of luminescence spectra of autunite [$Ca(UO_2)_2(PO_4)_2 \cdot 6.5H_2O$] which is typical of luminescent uranium minerals comprising hexavalent uranyl ion. The major absorption peaks are labelled A, B, C, D and E and the wavelengths at whcih these peaks occur are 3920 Å, 4020 Å, 4125 Å, 4245 Å and 4375 Å respectively. The major luminescence peaks are labelled F, G, H and I and the wavelengths at which these peaks occur are 5018 Å, 5250 Å, 5482 Å and 5750 Å respectively.

Figure 3:
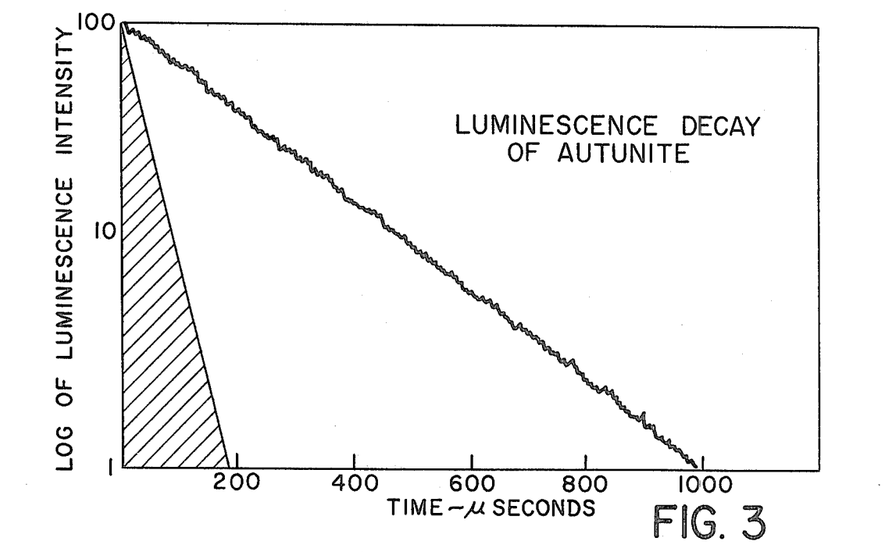
FIG. 3, on coordinates of intensity and time ($\mu$sec), depicts the period of luminescence decay of autunite following irradiation.

FIG. 3 is a plot showing the extended time in which the luminescence persists that is exhibited by a sample of autunite when it is illuminated for 0.008 microseconds with a laser beam having a wavelength of 4250 Å and the luminescence measured at 5250 Å, compared to most minerals (shaded region) when irradiated with ultraviolet light.

Figure 4:
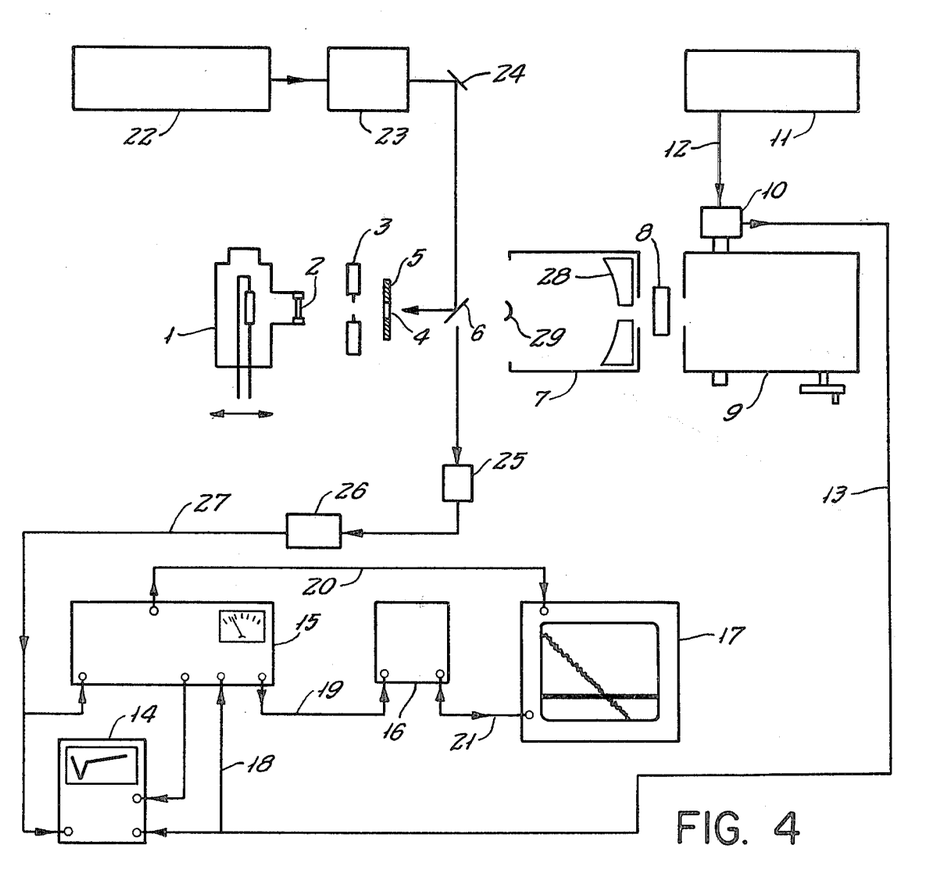
FIG. 4, is a block diagram of apparatus useful in the practice of the invention.

FIG. 4 is a block diagram of one equipment configuration used in the laboratory to obtain the luminescence spectrum (shown in FIG. 2 and the plot of the luminescence decay shown in FIG. 3) as well as to obtain absolute luminescence yields. Prior to measuring the luminescence emitted by sample 4, held in sample holder 5, the output from photomultiplier tube 10 is standardized by means of the radiant output of a calibrated lamp 1, a portion of whose output is emitted through a quartz optical window 2, and iris diaphragm 3. After calibration, the lamp is removed.

The plot of the luminescence decay time is obtained on X-Y recorder 17, by illuminating a sample 4 with light from nitrogen laser 22 and wavelength tunable dye laser 23, reflected onto sample 4, by means of mirrors 24 and 6. The lasers are adjusted to deliver light having a wavelength of 4250 Å and the total time of illumination is maintained for 0.008 microseconds. A portion of the luminescence generated in the sample is collected by telescope 7, focused by means of the spherical Cassegrainian mirror 28, onto mirror 29, which directs the light through filter 8, which will not pass light having a wavelength shorter than 5000 Å into monochrometer 9, which is set to pass light at a wavelength of 5250 Å ± 20 Å into photomultiplier 10, powered by high-voltage supply 11. The laser beam activates photodiode 25, which is biased by supply 26, from which trigger line 27 carries the signal to boxcar integrator 15 and oscilloscope 14. The signal from photomultiplier 10, is carried by line 13 to oscilloscope 14 and boxcar integrator 15 which transmits a signal to the X axis of recorder 17 through line 20, and to the Y axis of recorder 17, through line 19, logarithmic amplifier 16, and line 21.

The brightness of the luminescence from the sample, which is a thin section of the mineral, is equal to the power radiated per area into a unit solid angle in terms of $watts\text{-}cm^{-2}\text{-}ster^{-1}$ and is equal to the product of the incident laser energy, times the fraction of the light that is absorbed, times the luminescence yield, times the rate of emission, times ($1/(4\pi)$). The power measured at the photomultiplier is equal to the product of the brightness, times the area of the sample, times the solid angle.

Figure 5:
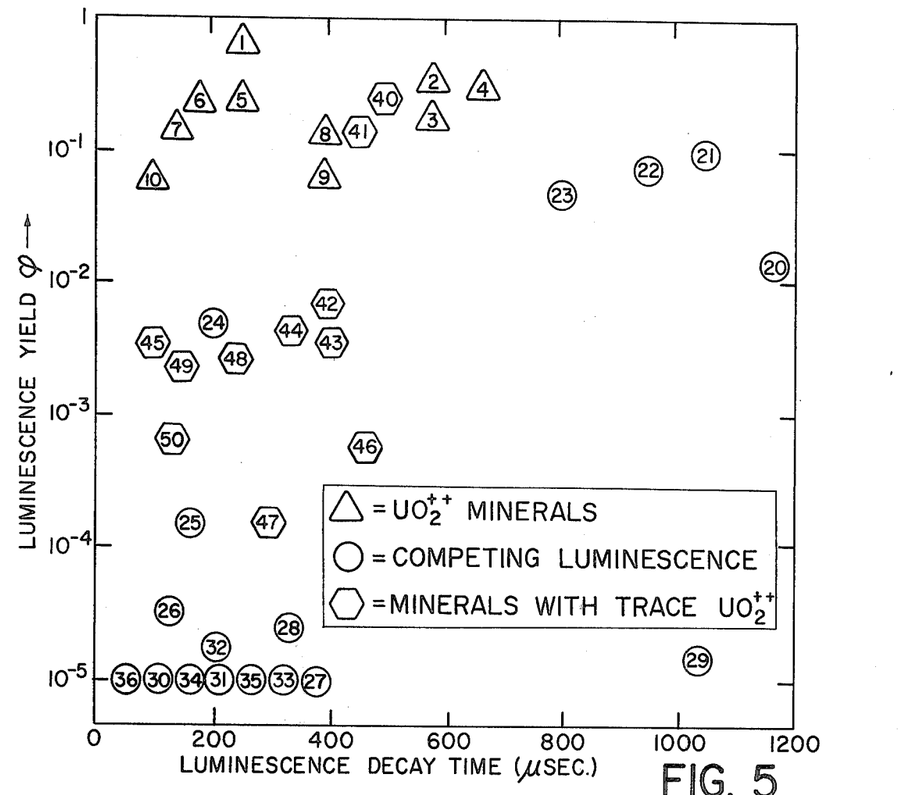
FIG. 5, on coordinates of luminescence yield and time ($\mu$sec), depicts the decay times for a variety of minerals excited by radiation having a wavelength of 4250 Å.

FIG. 5 shows the luminescence quantum yield, $\phi$, and the decay times for a variety of minerals comprising hexavalent uranyl ions (points 1–10) and non-uranyl minerals (points 20–36) when excited by radiation having a wavelength of 4250 Å. The luminescence yield $\phi$ is defined as the fraction of the absorbed energy which is radiated as luminescence. Points 20–24 are different samples of the phosphor, Willemite. Points 40–50 are non-uranium minerals which contain varying concentrations of uranyl ion as trace impurities. Examples are opals having the approximate formula $SiO_2 \cdot 0.2H_2O$. It can be seen that with few exceptions, the luminescence quantum yields of minerals comprising the uranyl ion are generally orders of magnitude larger than non-uranyl minerals when excited by light in the visible range.

Figure 6:
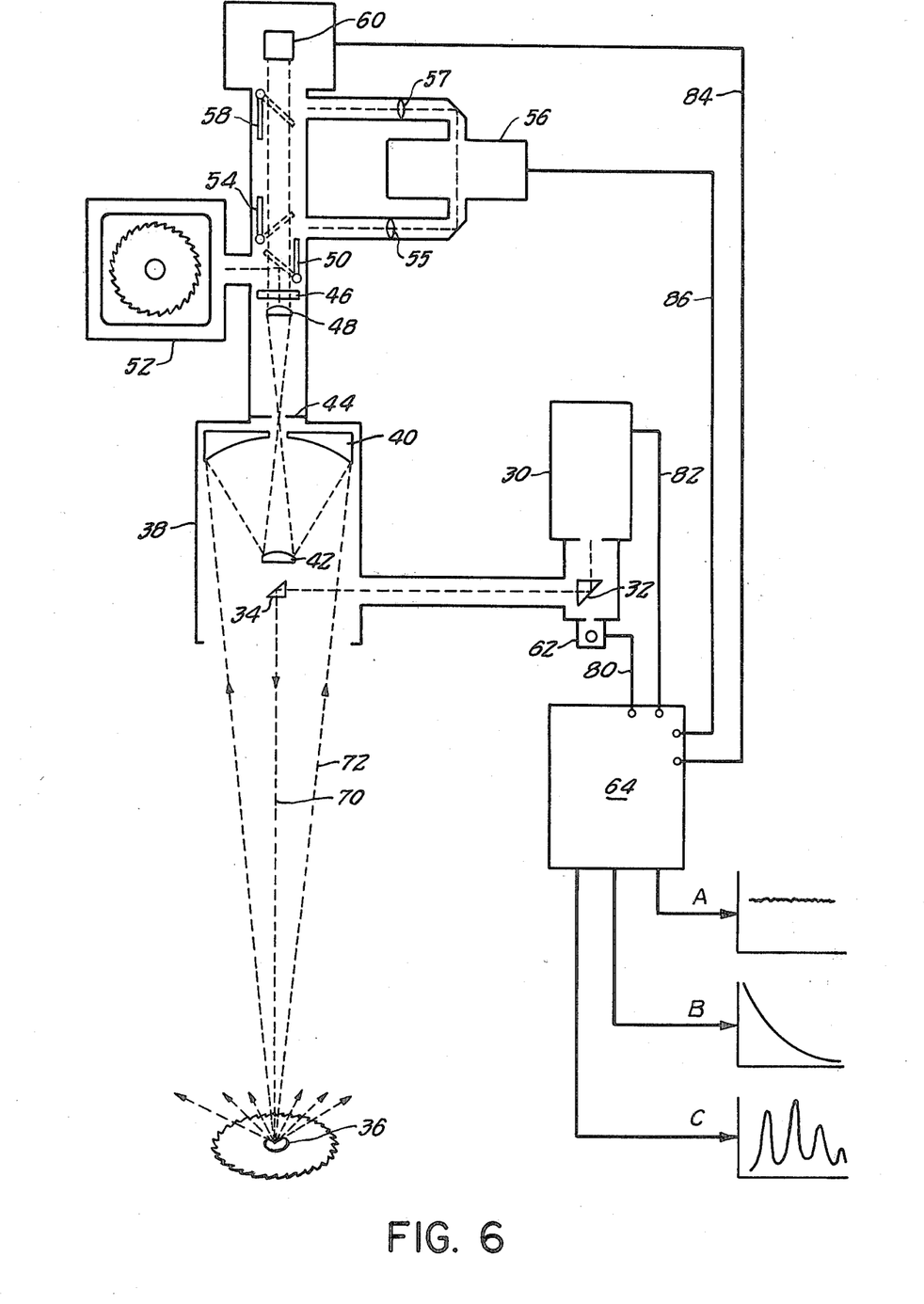
FIG. 6, shows a modification of the apparatus of FIG. 4 adapted for use from a remote platform such as airborne or truck.

FIG. 6 shows a modification of the equipment shown in FIG. 4, which has been adapted for use in the field, of a size and weight as to be readily accommodated in an airplane, helicopter, truck or other remote platform. A laser 30 transmits a beam of light, shown as dotted line 70, to a target area 36 located on terrain at ground level by means of prisms or mirrors 32 and 34 which latter is adjusted so that the laser beam be colinear with the optical axis of telescope 38, comprising mirrors 40 and 42. The transmitted lasser power is monitored by a photodiode 62.

The luminescence emitted by irradiated target 36, shown as dashed lines 72 is collected by mirror 40, focused on mirror 42 which projects the collected luminescence through iris 44 positioned at the back focal plane of the telescope, collimating lens 48, filter 46, and measured by photomultiplier tube 60, which transmits the information to computer 64 through line 84.

For purposes of alignment and photographic verification of the target area, the collimated light in the receiver may be diverted by means of a movable mirror 50 to an imaging device 52, such as a TV camera, film camera, or eye-piece.

For the purpose of obtaining luminescence spectra in the band width of the filter 46, mirrors 54 and 58 may be tilted to pre-set stops (shown dotted) and the collimated light focused by lens 55 into the scanning monochrometer 56. The dispersed light from the monochrometer may be recollimated by lens 57 and measured by the photodetector 60 and stored in computer 64 through line 86.

The entire measurement sequence is placed under control of the computer 64. A typical sequence involves: manual initiation in which the background light is measured, digitized and stored in the computer at a rate of 35–50 KHZ for a pre-set period of time. The computer then fires the laser through line 82 and the transmitted power measured by photodiode 62 is transmitted by line 80 to the computer and stored. After an adjustable time-delay which is equal to twice the propagation time for the laser beam to reach the target plus about 50 microseconds, the signal comprising the laser induced luminescence plus the background light in the same spectral band width is sampled for a duration of 1000 microseconds and stored in the computer. The computer automatically subtracts the previously sampled background signal and stores the laser-induced luminescence signal. If the signal-to-noise ratio exceeds a value of 25 the measurement sequence is complete. If the signal-to-noise ratio is less than 25, then the sequence is repeated and subsequent signals average over the sequence repetitions. Thus the equipment is used in a signal averaging mode.

Mode A, shown graphically in FIG. 6, would result in an operation in which the output, measured as luminescence intensity, is integrated over a present time period, say between 50 and 1000 microseconds.

Mode B, of the operation would result in a luminescence decay measurement with a temporal resolution between $(50\ KHz)^{-1}$ and $(35\ KHz)^{-1}$. The value of the time for which the intensity of the luminescence falls to $e^{-1}$ of the initial intensity, denoted herein as the "decay time", is thereby obtained.

Mode C of the operation results in a plot of the spectral characteristics of the luminescence. To do so, the computer steps the monochrometer to successive wavelengths and normalizes the measurement of the laser-induced luminescence to the power of the transmitted laser beam.

DESCRIPTION OF PREFERRED EMBODIMENTS

The wide variation in the chemical composition of uranyl minerals is given in Table I along with the fraction which luminesce.

TABLE I
| CHEMICAL TYPES OF URANYL MINERALS | |
|---|---|
| Type | Fraction Which Luminesces |
| Oxides | 0.14 |
| Carbonates | 0.36 |
| Sulfates | 0.50 |
| Arsenates | 0.44 |
| Phosphates | 0.35 |
| Vanadates | 0.0 |
| Silicates | 0.11 |

A sample of the worldwide occurence and distribution of these minerals as shown in Table II below and their similar temporal and spectral response to excitation by light having a wavelength of 4250 Å, followed by emission of luminescence at 5250 Å, as shown by FIGS. 1 through 3 for autunite suggest that this property is common to minerals comprising the hexavalent uranyl ion, and by means of a laser may be used to detect uranyl substances from a remote platform.

TABLE II
| OCCURRENCE OF SIGNIFICANT URANYL MINERALS IN HARD ROCK DEPOSITS | | | | | | | | | |
|---|---|---|---|---|---|---|---|---|---|
| Deposit Name | Location | Torber-nite | Autu-nite* | Urano-phane | Sklodow-skite | Gum-mite | Zippe-ite* | Salee-ite* | Kaso-lite |
| Midnite | Washington, USA | X | X | X | X | X | X | — | — |
| Schwartzwalder | Colorado, USA | X | X | X | — | — | X | — | — |
| Beaverlodge | N.W. Territory, Canada | — | — | X | X | — | X | — | X |
| Rabbit Lake | Saskatchewan, Canada | — | — | X | X | — | — | — | — |
| Mary Kathleen | Queensland, Australia | — | — | X | — | X | — | — | — |
| Jabiluka | N.W. Territory, Australia | — | X | — | X | — | — | X | — |
| Naborlek | N.W. Territory, Australia | X | X | — | X | X | — | X | — |
| Jabiru | Australia | — | — | — | — | — | — | X | — |
| Rossing | Nambia | X | — | X | — | X | — | — | — |
| Shinklowbe | Zaire | X | X | X | X | — | — | X | X |
| Linousin | France | X | X | X | — | X | — | — | — |

*Denotes luminescent minerals
X = Mineral present in Deposit
— = Mineral absent

Based on the experimental work disclosed herein, the essential features of a method for the detection of uranyl minerals comprise: (a) use of light having a narrow range of wavelengths in the 2400 to 5000 Å range, and preferably in the ranges of 2800 to 3500 Å and 3700 to 4500 Å for excitation; (b) measurement of the efficiency of the luminescence emitted by the excited mineral; (c) measurement of the luminescence decay time; and (d) measurement of the spectrum of the emitted luminescence.

These parameters, taken in combination, provide a novel "selective window" whereby the luminescence from minerals comprising the hexavalent uranyl ion may be distinguished from the luminescence of non-uranyl substances.

A major objective of this invention is the utilization of this "selective window" to detect substances, either in the natural state or in materials which have been physically or chemically processed, which comprise the hexavalent uranyl ion. For the remote detection of these substances, the equipment illustrated in FIG. 6 and variations thereof which are obvious to those skilled in the laser and electronic arts is particularly suitable.

The essential features of an instrument for the remote detection of minerals which include hexavalent uranyl ions in their composition comprises: (a) a transmitter comprised of a pulsed or chopped CW laser excitation source combined with an optical system to transmit the laser radiation to the target area to be sampled; (b) a receiver, comprised of an optical system to collect a portion of the emitted luminescence; (c) means for limiting the spectral band width of the collected luminescence by means of filters or a monochrometer and converting the collected luminescence to an electric signal by means of a gated photodetector; (d) a data handling system to provide a means to record and display the acquired signal and record distance of light source to target area, background light and noise and speed of motion of the detector relative to the target or means for automatically maintaining the detector focused on the target for about 1000 microseconds after termination of irradiation; and (e) means for reducing the data to equivalent uranium concentration. The data handling system would record the spectral distribution, intensity and the time decay of the emitted luminescence.

In a preferred embodiment, the laser is operated to emit a pulse of radiation for a duration of less than 100 microseconds at a wavelength in the range of about 2400 to 5000 Å, preferably in the ranges of about 2800 to 3500 Å or 3700 to 4500 Å for ground sampling and in the range of about 4200 to 5000 Å for water sampling. The detector will be "gated on" after a time interval, following termination of the irradiation, comprised of twice the propagation time of the laser light from the transmitter to the target, plus about 50 microseconds, and will be maintained in a "gated on" state for no more than about 1000 microseconds.

Examples of laser sources useful in the practice of the invention include a rare gas-halide laser operating at 3080 Å (e.g., XeCl), a frequency-shifted KrF laser operating at 2490 Å and a flashlamp-pumped dye laser at 4250 Å.

Alternative methods to pulsed illumination of the target and gated detection of the luminescence emitted by the target may be employed to take advantage of the long fluorescence lifetime of uranyl minerals and thereby selectively detect their occurence.

For example, a continuous wave laser or other light source operating in the wavelength range of 2400 to 5000 Å can be modulated, say sinusoidally, at a frequency, w. If the target contains only the uranyl mineral, then the fluorescence response to the sinusoidal illumination will also be sinusoidal at frequency, w, with an amplitude and phase shift which depends upon both w and the inverse of the fluoroscence lifetime, $\gamma (\gamma = 1/\tau_{fluorescence})$. Explicitly, the phase shift, $\phi$, is given by $$\phi = \tan^{-1} w/\gamma$$

If the fluorescence is detected synchronously at w, a constant voltage will result which is proportional to the cosine of the phase shift, $\cos \phi$, and also proportional to other factors involving $\gamma$ and w. This is a well-known technique to determine the fluorescence lifetime by measurement of $\phi$.

If the sample area now contains both the fluorescent uranyl mineral as well as a second fluorescent non-uranyl mineral with inverse fluorescence lifetimes of $\gamma_u$ and $\gamma_x$, respectively, where $\gamma_x >> \gamma_u$, then the phase shift of the fluorescent response, $\phi$, is given by $$\phi = \tan^{-1} \left[ \frac{w}{w^2 + \gamma_u^2} + \frac{w}{w^2 + \gamma_x^2} \right] \left[ \frac{\gamma_u}{w^2 + \gamma_u^2} + \frac{\gamma_x}{w^2 + \gamma_x^2} \right]^{-1}$$

In the above expression, it is assumed for simplicity that both species are present in equal concentrations and they have the same absorption cross sections for the incident radiation. Again, the output of a synchronous detector is proportional to $\cos \phi$ and other factors of $\gamma_u$, $\gamma_x$, and w. By choosing the modulation frequency, w, to be less than or equal to $2\pi\gamma_u$, the contributions to the total detector output of the fluorescent minerals with shorter lifetimes can be minimized and, in fact, can be reduced to less than 10% of the total signal for conditions mentioned above.

Suitable lasers are for example He-Cd at 4461 Å and Ar$^+$-pumped dye lasers.

EXAMPLE 1

A thin section of meta-autunite was prepared and its optical and luminescence properties determined. The results are given in Table III.

TABLE III

| OPTICAL PROPERTIES OF AUTUNITE | |
|---|---|
| Sample thickness, L(cm) | $35 \times 10^{-4}$ cm |
| Wavelength for max. absorption, $\lambda_E$(Å) | 4250A |
| Absorption coefficient at $\lambda_E$, $\alpha$(cm$^{-1}$) | 381 cm$^{-1}$ |
| Room Temp. Lifetime, $\gamma^{-1}$ (sec) | $227 \times 10^{-6}$ sec |
| Luminescence Yield, $\phi = \gamma\ 77°\ K./\gamma 298°\ K.$ | 0.80 |

It can be shown that for this example the brightness (B) of the sample when illuminated is given by the equation:

$$B = \bar{P}_L \tau_L (1 - e^{-\alpha L}) \phi \gamma (\tfrac{1}{4}\pi)$$

where L is the thickness of the sample in cm; $\bar{P}_L$ is the intensity in (watts-cm$^{-2}$) of the illumination from a pulsed laser; $\tau_L$ is the duration of illumination in seconds and B is the brightness (in watts-cm$^{-2}$-ster$^{-1}$) of the luminescence.

Substituting the data in Table III, $$B = 8.5 \times 10^{-4}\ \text{watts-cm}^{-2}\text{-ster}^{-1}$$

where $P_L$ is equal to 800 watts-cm$^{-2}$ and $\tau_L$ is equal to $8 \times 10^{-9}$ seconds. Actual measurement of the brightness using the above conditions gave a value for the brightness of $1 \times 10^{-3}$ watts-cm$^{-2}$-ster$^{-1}$ which is in good agreement with the measurements listed in Table III.

Figure 7:
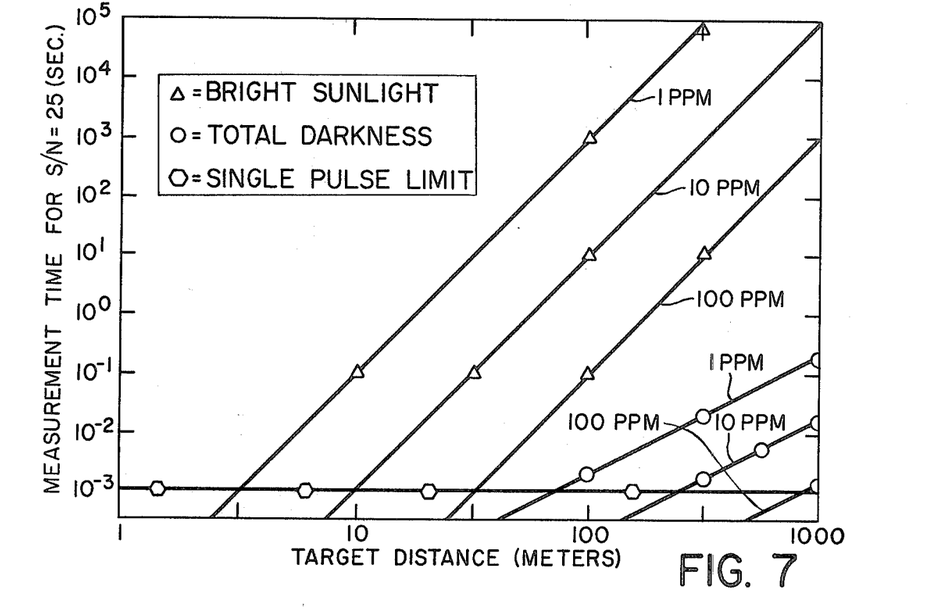
FIG. 7, on coordinates of time (μsec) and distance (m), depicts the measurement time required to achieve a signal-to-noise power ratio of 25 for various surface area concentrations in parts per million at various distances under various conditions.

FIG. 7 is a plot showing the measurement time in seconds required at a signal-to-noise power ratio of 25 for various surface area concentrations of autunite in parts per million at various distances, in bright sunlight and total darkness when illuminated with a laser having a power of 100 kw; a wavelength of 4250 Å; a pulse width of $150 \times 10^{-9}$ sec.; a repetition rate of 30 pps; and a divergence of $4 \times 10^{-3}$ radians, using a receiver having a diameter of 17 cm and a sampling time of 400 microseconds. The calculations are based on sunlight having a maximum power of $10^{-2}$ watts-cm$^{-2}$, and all noise sources in total darkness being less than $5 \times 10^5$ photons-sec$^{-1}$. From the above it is seen that the measurement time is dependent upon the distance from the laser to the target area and the area concentration of autunite.

With reference to FIG. 7, the single-pulse limit of $10^{-3}$ seconds is determined by the longest decay time for a uranyl mineral. It can be seen that when autunite is present at a concentration of 100 ppm, it can be detected at night at a distance of 1000 meters with a single pulse from the laser transmitter used for the data in FIG. 7.

EXAMPLE 2

The following materials exhibit the characteristics of the uranyl ion when excited by light in the wavelength range from 2800 to 4900 Å; chalcedony, opal (Nevada), hyalite opal, opalite, autunite, andersonite, liebigite and schroekingerite.

Data taken at shorter wavelengths of absorption were taken with a Spex spectrophotometer on a wide variety of minerals containing the uranyl ion. The absorption spectra were determined by varying the wavelength of the excitation light source and recording the intensity of the fluorescence which is emitted at 5250 or 5500 Å normalized to the intensity of the excitation light source. The excitation was varied from 2700 Å or 3000 Å, with a few samples studied at wavelengths from 2500 Å.

The data are summarized in Table IV below, which lists the sample identification, description, measured wavelength range of absorption and wavelength of observed absorption maximum below 4250 Å ($\gamma_m$).

| SAMPLE ID | DESCRIPTION | RANGE OF ABSORPTION (Å) | $\gamma_m$ (Å) |
|---|---|---|---|
| U-234 Autunite | Utah naturally occuring surface uranyl mineral | 2000–5000 | 3000 |
| U-167 Schroekingerite | pure mineral in SiO$_2$ powder | 2500–4800 | 2700 |
| U-131 Andersonite | pure mineral in SiO$_2$ powder | 2500–4900 | 3100 |
| U-119 Autunite | pure mineral in SiO$_2$ powder | 3000–5000 | 3000 |
| U-141 Liebigite | | | 3000 |
| U-219 Autunite | Conn. mineral flakes on artificially fractured surface | 3000–5000 | 3000 |
| U-235 Tyuyamunite | Utah naturally occuring surface uranyl mineral | 2500–5000 | 2500 |
| U-232 Uranophane | N.M. naturally occuring surface uranyl mineral | 2500–5000 | 2500 |
| U-239 Calcite -233 and | Dilute uranyl as impurity from Ariz., N.M., and Utah | 2800–5000 | 2900 |
| Opal -238 | | 2500–5000 | 2500 |
| U-250 Opal | Nev. not so dilute uranyl as impurity in transparent host | 2500–5000 | 2500 |
| U-240 Opalite | Nev. | 3000–5000 | 3000 |
| U-241 Mahogany Opalite | Not so dilute uranyl as impurity in absorbing matrix | 3000–4500 | 3000 |
| U-244 Diatomaceous earth | Not so dilute uranyl in non absorbing, strongly scattering matrix | 3000–5000 | 3000 |
| U-243 Coating on -246 Rhyolite | Nev. Dilute uranyl impurity in silica matrix | 3000–5000 | 3000 / 3000 |
| U-263 Quartz- -253 jaspilite- -264 hematite -266 brescia -269 -256 | Wyoming | 2700–5000 | 2700 |
| U-280 Calcrete -281 chalcedony -278 -276 -279 | White River formation, Wyoming | 2700–5000 | 2700 |

What is claimed is:

1. Method for detecting the presence of uranium in a substance present in a target area in which the uranium is present in said substance as a hexavalent uranyl ion which comprises:
    (a) irradiating said target area with light from a light source, said light having a wavelength in the range of about 2400 to 5000 Å for a period of time equal to or less than about 100 microseconds to induce luminescence in said substance;
    (b) waiting for a period of time equal to twice the propagation time for the light to travel from said light source to said target, plus about 50 microseconds; and
    (c) measuring the intensity, decay time and spectral distribution of said luminescence.

2. Method according to claim 1 wherein said light is a laser beam having a wavelength in the range of 3700 to 4500 Å and said light source is a laser generator.

3. Method according to claim 1 wherein said light is a laser beam having a wavelength in the range of about 2800 to 3500 Å and said light source is a laser generator.

4. Method according to claim 1 wherein said measurement of the luminescence intensity, decay time and spectral distribution is over a period of about 50 to 1000 microseconds.

5. Method according to claim 1 wherein the initial intensity of said luminescence is in the ratio of at least about 25 to 1 over the background radiation noise and other sources of noise.

6. Method according to claim 1 wherein said decay time is equal to the time for the intensity to decrease to $e^{-1}$ of the initial intensity of said luminescence.

7. Method according to claim 1 wherein said measurement of the spectral distribution of said luminescence is in the range of about 5000 Å to 6000 Å.

8. Method according to claim 1 wherein said substance is a mineral selected from the group consisting of autunite, zippeite and saleeite.

9. Method according to claim 1 wherein said target area is part of the terrain and said light source is located remote from said terrain.

10. Method for detecting the presence of surface deposits of uranium minerals comprising hexavalent uranyl ions in a target area remote from an observation point comprises:
    (a) irradiating said target area with a beam of light having a wavelength in a range from 2800 to 3500 Å as 3700 to 4500 Å emitted by a laser positioned at said observation point for a period of time equal to or less than about 100 microseconds;
    (b) waiting for a period of time equal to twice the time required for the propagation of said light from said laser to said target area, plus about 50 microseconds; and
    (c) measuring the intensity and the decay time at a wavelength of 5250 Å, by means of an optical receiver, for a period of up to 1000 microseconds the luminescence induced in said mineral by said irradiation.

11. An apparatus for the remote detection of uranium minerals which emit luminescence when irradiated with light having a wavelength in the range of about 2400 to 5000 Å, said minerals being located at a target area at ground level, which comprises:
    (a) a transmitter comprised of a laser excitation source emitting light in the range of about 2400 to 5000 Å in combination with an optical system to transmit the laser radiation to the target area;
    (b) a receiver, comprised of an optical system to collect a portion of the emitted luminescence;
    (c) means for limiting the spectral band width of the collected luminescence and converting the luminescence to an electric signal by means of a gated photomultiplier;
    (d) a data handling system to provide means to record the distance of the light source to the target area; background light and noise and means for automatically maintaining the detector focused on the target for about 1000 microseconds after termination or irradiation; and
    (e) means for recording the intensity, decay time and spectral distribution of the luminescence and converting these data to uranium concentration.

12. The apparatus of claim 11 in which said wavelength is in the range of about 3700 to 4500 Å.

13. The apparatus of claim 11 in which said wavelength is in the range of about 2800 to 3500 Å.

14. The apparatus of claim 11 in which the laser excitation source emits continuous wave radiation.

15. The apparatus of claim 14 in which the continuous wave radiation is pulsed or chopped.

16. The apparatus of claim 14 in which the continuous wave radiation is modulated.

* * * * *